United States Patent
Singh et al.

(10) Patent No.: US 11,198,649 B2
(45) Date of Patent: Dec. 14, 2021

(54) METHOD FOR DESIGNING FOR COMPRESSIVE STRENGTH FOR CEMENT SLURRY

(71) Applicant: Halliburton Energy Services, Inc., Houston, TX (US)

(72) Inventors: John Paul Bir Singh, Kingwood, TX (US); Thomas Jason Pisklak, Cypress, TX (US); Ronnie Glen Morgan, Waurika, OK (US)

(73) Assignee: Halliburton Energy Services, Inc., Houston, TX (US)

(*) Notice: Subject to any disclaimer, the term of this patent is extended or adjusted under 35 U.S.C. 154(b) by 84 days.

(21) Appl. No.: 16/633,411

(22) PCT Filed: Apr. 5, 2019

(86) PCT No.: PCT/US2019/026179
§ 371 (c)(1),
(2) Date: Jan. 23, 2020

(87) PCT Pub. No.: WO2020/204959
PCT Pub. Date: Oct. 8, 2020

(65) Prior Publication Data
US 2021/0171408 A1 Jun. 10, 2021

(51) Int. Cl.
*C04B 40/00* (2006.01)
*G06F 30/20* (2020.01)
*C04B 28/04* (2006.01)
*C04B 28/14* (2006.01)
(Continued)

(52) U.S. Cl.
CPC .......... *C04B 40/0032* (2013.01); *C04B 28/04* (2013.01); *C04B 28/14* (2013.01);
(Continued)

(58) Field of Classification Search
CPC ..... C04B 40/0032; C04B 28/04; C04B 28/14; C04B 2201/50; G06F 30/20;
(Continued)

(56) References Cited

U.S. PATENT DOCUMENTS

| 2010/0212892 | A1* | 8/2010 | Santra | C04B 28/32 |
| | | | | 166/250.14 |
| 2017/0364607 | A1* | 12/2017 | Kaushik | G16C 60/00 |
| 2019/0040297 | A1* | 2/2019 | Terrier | C09K 8/428 |

FOREIGN PATENT DOCUMENTS

| KR | 101091871 | 12/2011 |
| KR | 101346560 | 1/2014 |

OTHER PUBLICATIONS

Sang-Hun Han, Jin-Keun Kim, Yon-Dong Park. (2003). Prediction of compressive strength of fly ash concrete by new apparent activation energy function. Cement and Concrete Research, vol. 33(7), pp. 965-971, https://doi.org/10.1016/S0008-8846(03)00007-3. (Year: 2003).*

ISRWO International Search Report and Written Opinion for PCT/US2019/026179 dated Jan. 3, 2020.

K. S. Pann, et al., New Strength Model Based on Water-Cement Ratio and Capillary Porosity, ACI Materials Journal. vol. 100, 2003.

(Continued)

*Primary Examiner* — Crystal J Miller
(74) *Attorney, Agent, or Firm* — Thomas Rooney; C. Tumey Law Group PLLC

(57) ABSTRACT

A method of designing a cement slurry may include: providing a cement slurry recipe comprising water and at least one cementitious component; creating a model of a compressive strength of the cement recipe for a given time; preparing a cement slurry based at least in part on the model; and introducing the cement slurry into a subterranean formation.

17 Claims, 5 Drawing Sheets

(51) Int. Cl.
   *C09K 8/46* (2006.01)
   *E21B 33/14* (2006.01)
   *G01N 3/08* (2006.01)
   *G01N 33/38* (2006.01)
   *G06F 111/10* (2020.01)

(52) U.S. Cl.
   CPC ............... *C09K 8/46* (2013.01); *E21B 33/14* (2013.01); *G01N 3/08* (2013.01); *G01N 33/383* (2013.01); *G06F 30/20* (2020.01); *C04B 2201/50* (2013.01); *E21B 2200/20* (2020.05); *G01N 2203/0019* (2013.01); *G06F 2111/10* (2020.01)

(58) Field of Classification Search
   CPC .... G06F 2111/10; G01N 3/08; G01N 33/383; G01N 2203/0019; E21B 33/14; E21B 2200/20; C09K 8/46
   See application file for complete search history.

(56) References Cited

OTHER PUBLICATIONS

PCT Application No. PCT/US2019/026167 dated Apr. 5, 2019.
Han et al., Prediction of compressive strength of fly ash concrete by new apparent activation energy function. Cement and Concrete Research. Jul. 2003.
Yang et al., Apparent Activation Energy for Predicting Compressive Strength of Concrete Using Blast Furnace Slag. Applied Mechanics and Materials. May 2015.

\* cited by examiner

METHOD FOR DESIGNING FOR COMPRESSIVE STRENGTH FOR CEMENT SLURRY

BACKGROUND

In well cementing, such as well construction and remedial cementing, cement compositions are commonly utilized. Cement slurries may be used in a variety of subterranean applications. For example, in subterranean well construction, a pipe string (e.g., casing, liners, expandable tubulars, etc.) may be run into a well bore and cemented in place. The process of cementing the pipe string in place is commonly referred to as "primary cementing." In a typical primary cementing method, a cement slurry may be pumped into an annulus between the walls of the well bore and the exterior surface of the pipe string disposed therein. The cement slurry may set in the annular space, thereby forming an annular sheath of hardened, substantially impermeable cement (i.e., a cement sheath) that may support and position the pipe string in the well bore and may bond the exterior surface of the pipe string to the subterranean formation. Among other things, the cement sheath surrounding the pipe string functions to prevent the migration of fluids in the annulus, as well as protecting the pipe string from corrosion. Cement slurries also may be used in remedial cementing methods, for example, to seal cracks or holes in pipe strings or cement sheaths, to seal highly permeable formation zones or fractures, to place a cement plug, and the like.

A particular challenge in well cementing is the development of satisfactory mechanical properties in a cement slurry within a reasonable time period after placement in the subterranean formation. Oftentimes several cement slurries with varying additives are tested to see if they meet the material engineering requirements for a particular well. The process of selecting the components of the cement slurry are usually done by a best guess approach by utilizing previous slurries and modifying them until a satisfactory solution is reached. The process may be time consuming and the resulting slurry may be complex. Furthermore, the cement components available in any one particular region may vary in slurry from those of another region thereby further complicating the process of selecting a correct slurry.

BRIEF DESCRIPTION OF THE DRAWINGS

These drawings illustrate certain aspects of some of the embodiments of the present disclosure and should not be used to limit or define the disclosure.

DETAILED DESCRIPTION

Figure 1:
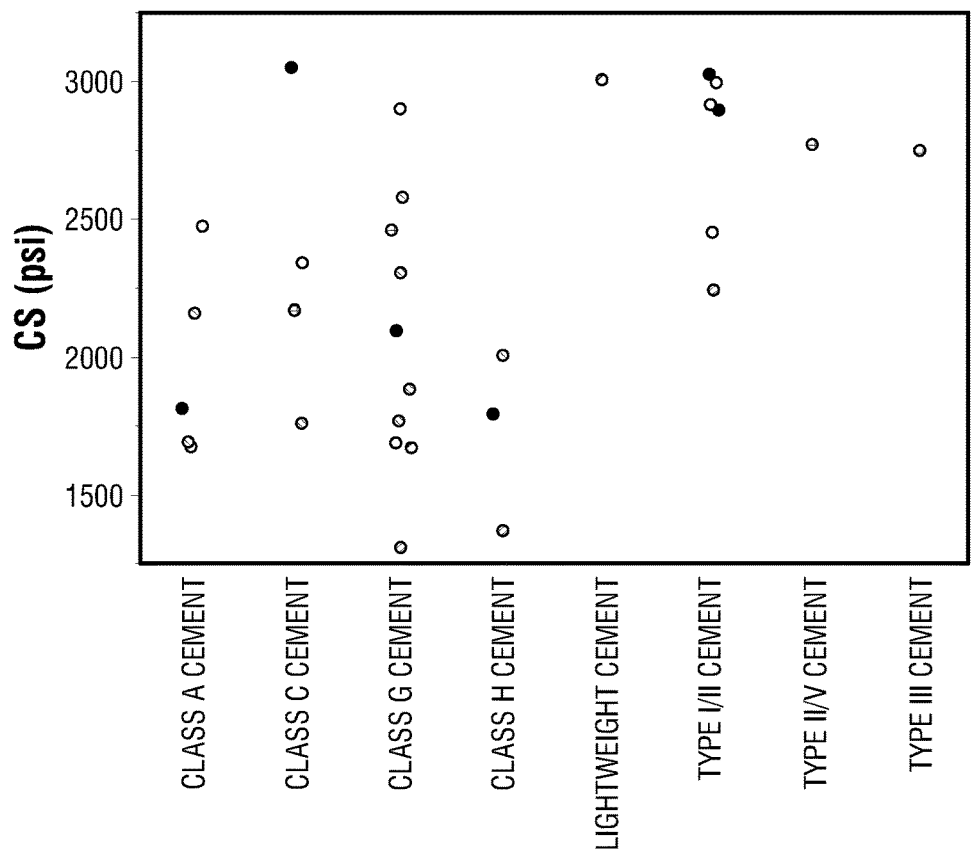
FIG. 1 illustrates a compressive strength test for a variety of cement types from different manufacturers and regions.

The present disclosure may generally relate to cementing methods and systems. More particularly, embodiments may be directed to designing cement slurries based at least partially on modeling of compressive strength.

One common type of cement used in wellbore and surface cementing is Portland cement. Portland cement may be available in several classes and types which are provided to guide selection of cements. The ASTM International Standard Organization has designated five types of Portland cement, designated types I-V. The ASTM defines each class based on several factors including, but not limited to, fineness or average particle size and chemical makeup. The API (American Petroleum Institute) publishes standards for Portland cement in API Spec. 10A, which lists classes of Portland cement as class A, class B, class C, class G, and class H. A first step in designing a cement slurry may be to select the type of Portland cement, whether by API class or ASTM type, to include in the cement slurry. While the class or type of Portland may give an indication to one of ordinary skill in the art some properties of the Portland cement, the wide variety of availability of Portland cements and distribution of performance characteristics thereof make the class or type an inadequate indicator of actual performance. As will be illustrated herein, regional and manufacturer variability in Portland cement can make selection based on type or class an inexact measure of actual performance. This may lead to a large number or slurry designs to be developed and tested before a suitable slurry is found for a particular application.

Provided herein are methods that may include designing cement slurries, sometimes referred herein as cement slurries, with a model of Portland cement compressive strength. A model of compressive strength may include time and temperature dependencies of compressive strength and may be applicable to cement slurries with only Portland cement, also called a neat Portland cement design, as well as to cement slurries with reduced Portland cement content, such as those slurries which include other cementitious components in addition to Portland cement. The methods may allow one of ordinary skill in the art, with the benefit of this disclosure, to design cement slurries containing Portland cement with a reduced number of iterations to reach a cement slurry with required mechanical properties for a particular application. The methods presented herein may be advantageous over traditional trial-and-error based cement slurry design processes as the trial-and-error methodology, while generally effective at finding a workable cement slurry, may be inefficient and time consuming and may result in a cement slurry that has certain undesirable characteristics. Some undesirable characteristics may include number of components in the cement slurry, concentrations of components in the cement slurry, excessive compressive strength beyond engineering requirements, complexity of the cement slurry, and others readily recognized by those of ordinary skill in the art. Further uses of the methods and systems described herein may be in automation of wellbore cement slurry design.

FIG. 1 illustrates a compressive strength test for a variety of cement types from different manufacturers and regions, including class A Portland cement, class C Portland cement, class G Portland cement, class H Portland cement, lightweight cement, type I/II Portland cement, type II/V Portland cement, and type III Portland cement. In FIG. 1 the horizontal axis is the cement type, the vertical axis is the compressive strength in PSI, and each dot in a horizontal line represents a slurry prepared with the type of cement indicated on the horizontal axis from different manufacturers. The cement slurries were prepared and cured at 140° F. (60° C.) for 7 days and subjected to unconfined compressive strength testing. From FIG. 1, it can be seen that there is no correlation between the compressive strength a neat Portland cement slurry develops, and the class/type of Portland cement used to prepare the slurry.

Compressive strength of a cement slurry may be correlated with a mass of water to mass of cementitious material ratio (w/c). In general, two try blend cement slurries mixed with unequal amounts of water may exhibit different final compressive strengths. A cement slurry prepared with relatively more water or a higher w/c ratio may have a lower final compressive strength than a cement slurry prepared with relatively less water or a lower w/c ratio. The relationship between compressive strength and w/c ratio may be described by Abrams' law in equation 1. Alternatively, equation 1 may be rewritten in log form as in equation 2, for example. The constants A and B may be may vary depending on the identity of the cementitious material. Constants for fly ash may not be identical to constants associated with Portland cement. Furthermore, the constants A and B may also vary depending on the source of the cementitious material as individual manufacturer processes may result in variations in mineralogical makeup of cementitious materials. For natural or mined materials such as natural glasses, regional variability may result from different mines or natural source of the materials.

Equation 1 may be used to predict compressive strengths of Portland cement slurries as well as cements that do not comprise Portland cement. Equations 1 and 2 may also be used for cements such as pozzolanic cements, aluminate cements, geopolymer cements, and others. Equations 1 and 2 may also be used for blends of cementitious materials, such as Portland and a second cementitious material, if the interaction between the constants A and B for Portland cement and the constants A and B for the second cementitious material are known.

$$CS = \frac{A}{B^{1.5*(\frac{w}{c})}} \quad (1)$$

$$\ln(CS) = \ln(A) - 1.5*\ln(B)*\frac{w}{c} \quad (2)$$

Figure 2:
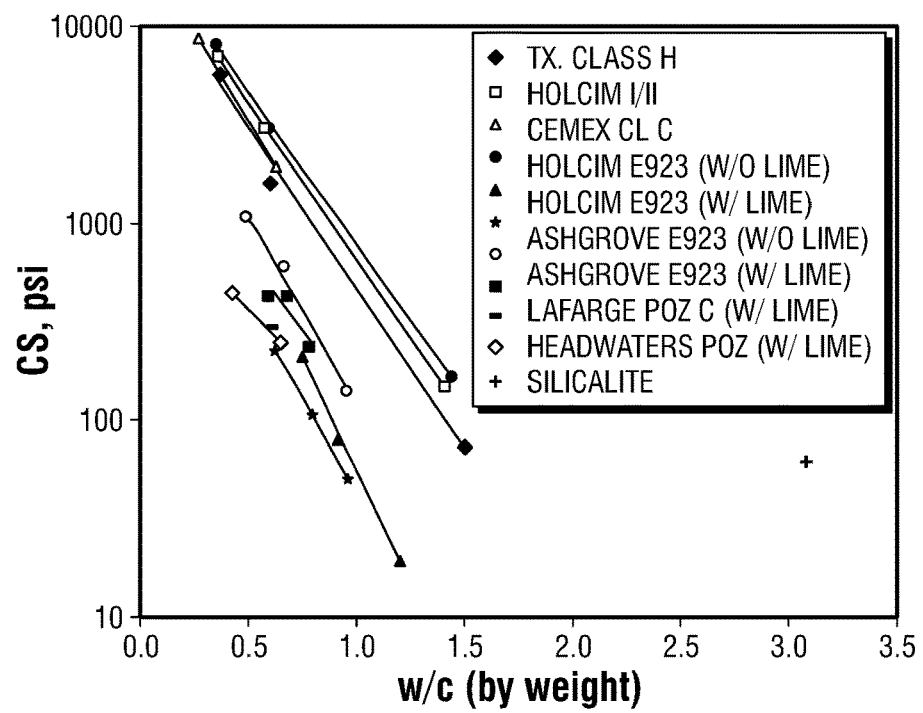
FIG. 2 illustrates results of a compressive strength test.

To demonstrate variability between different sources of cementitious materials and to test the viability of equation 1 for cementitious materials, a series of compressive strength tests were performed using a variety of cementitious materials from different manufacturers. Cement slurries were prepared with 11 different cementitious materials and varying amounts of water to cement ratios. Each of the slurries included only one cementitious material and water. The water to cement ratios were varied between 0.5 and 1.5. Each of the slurries was cured at 140° F. (60° C.) for 7 days. A compressive strength test was performed on each of the cured cement slurries, the results of which was illustrated in FIG. 2. The compressive test results in FIG. 2 indicate that the log-linear relationship between compressive strength and w/c ratio appear to hold for tested values of w/c from 0.5 to 1.5. It may be concluded that the compressive strength is exponentially related to the mass ratio of water to cementitious material.

A second set of compressive strength tests was performed using blends of cementitious materials and water. Blends of cementitious materials were prepared by selecting cementitious materials from the group of Portland cement fly ash, silica fume, and cement kiln dust in varied weight ratios. Slurries were prepared with each of the blends of cementitious materials. The water to cement ratios were varied between 0.5 and 1.5. one cementitious material and water. Each of the slurries was cured at 140° F. (60° C.) for 7 days. A compressive strength test was performed on each of the cured cement slurries, the results of which was illustrated in FIG. 3. The compressive test results in FIG. 3 indicate that the log-linear relationship between compressive strength and w/c ratio appear to hold for blends of cementitious materials tested at values of w/c from 0.5 to 1.5. It may be concluded that the compressive strength is also exponentially related to the mass ratio of water to cementitious material for blends of cementitious materials.

Power law behavior of water to cement ratios on compressive strength may be approximated by an exponential equation. Equation 3 is a model that may approximate the behavior of a cement slurry as a function of $CS_0$, w/c, and a constant n. Equation 3 may predict the ultimate compressive strength of the cement slurry. Alternatively, equation 3 may be rewritten as equation 4. $CS_0$ is the compressive strength obtained when water and cement are mixed in equal mass proportions (w/c=1) and n is function of various factors such as, including, but not limited to, time of cure, temperature of curing, slurry of dry cement blend, and other factors. From the results it can be observed that the value of n may be on the order of about −2.5 for various cementitious system. The cement in the water to cement ratio is any cementitious material such as fly ash, cement kiln dust, Portland cement, natural glass, and other cementitious materials that may be present in the cement slurry. The water to cement ratio w/c can also be calculated from slurry density ($\rho_s$), dry blend density ($\rho_D$), and water density ($\rho_w$) as shown in equation 5.

$$CS = CS_0\left(\frac{w}{c}\right)^n \quad (3)$$

$$\ln\left(\frac{CS}{CS_0}\right) = n*\ln\left(\frac{w}{c}\right) \quad (4)$$

$$\frac{w}{c} = \frac{1 - \frac{\rho_s}{\rho_D}}{\frac{\rho_s}{\rho_w} - 1} \quad (5)$$

Equations 2 and 5 may be combined to form equation 6 and equations 5 and 4 may be combined to form equation 7. Equations 6 and 7 may be used to predict compressive strength for any known values of A and B.

$$\ln(CS) = \ln(A) - 1.5*\ln(B)*\frac{1 - \frac{\rho_s}{\rho_D}}{\frac{\rho_s}{\rho_w} - 1} \quad (6)$$

$$\ln\left(\frac{CS}{CS_0}\right) = n*\ln\left(\frac{1 - \frac{\rho_s}{\rho_D}}{\frac{\rho_s}{\rho_w} - 1}\right) \quad (7)$$

A generalized correlation for 7-day compressive strength, also known as the ultimate compressive strength, may be written as in question 8.

$$CS(7\text{-day}) = f(WR, SG, \text{particle size}, BET, SSA, C_2S, C_3S, C_4AF, C_3A, CaSO_4, \text{gypsum}) \quad (8)$$

Figure 3:
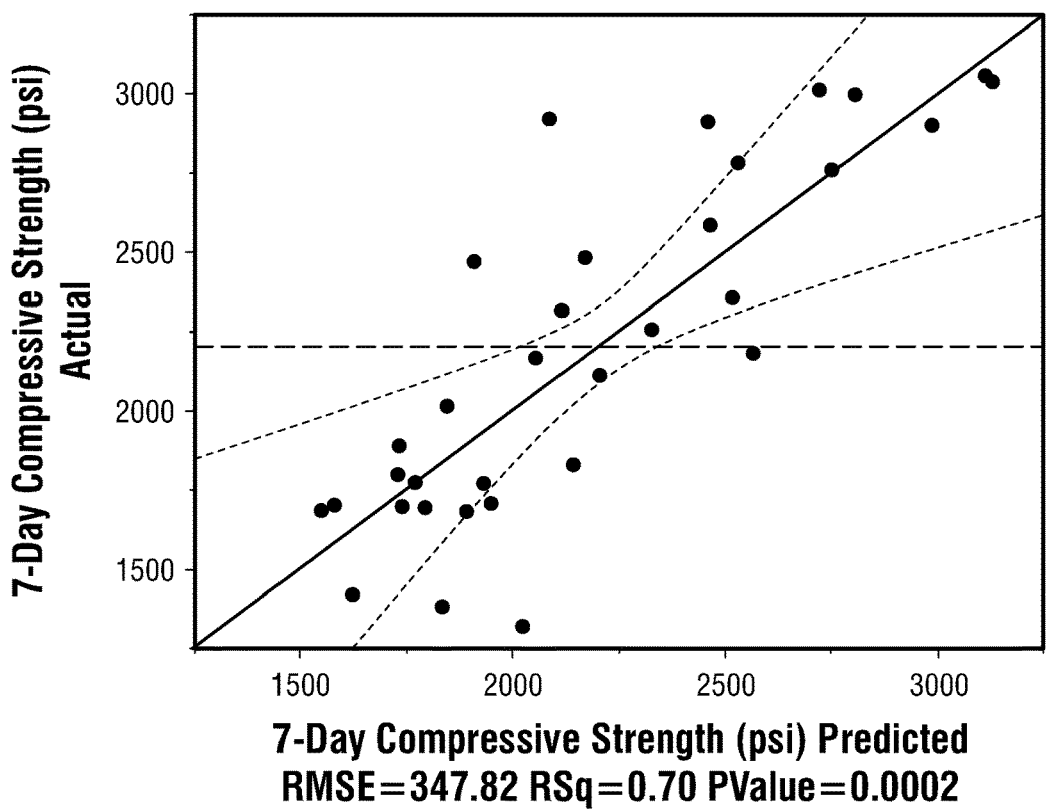
FIG. 3 illustrates results of a compressive strength test.

In equation 8, CS(7-day) is the 7 day compressive strength of the cement slurry, WR is the water requirement of the cement components in the cement slurry, SG is the specific gravity of the cement components in the cement slurry, particle size is the particle size of the cement components in the cement slurry, BET is the Brunauer-Emmett-Teller surface area of the cement components in the cement slurry, SSA is the specific surface area of the cement components in the cement slurry, $C_2S$ is the concentration of dicalcium silicate of the cement components in the cement slurry, $C_3S$ is the concentration of tricalcium silicate of the cement components in the cement slurry, $C_4AF$ is the concentration of tetra calcium aluminoferrite of the cement components in the cement slurry, $C_3A$ is the concentration of tricalcium aluminate of the cement components in the cement slurry, $CaSO_4$ is the concentration of calcium sulfate of the cement components in the cement slurry, and gypsum is the concentration of gypsum of the cement components in the cement slurry. Using equation 8 with equation 3 allows the prediction of a 7-day strength for any neat Portland cement slurry. FIG. 3 is a graph illustrating the predicted versus observed 7-day compressive strength for neat Portland cement slurries.

The hydration of Portland cement releases energy as heat. The heat released may increase the temperature of the Portland cement slurry which in turn may accelerate the hydration reactions in the Portland cement slurry. A study was performed to characterize the calorimetric effects of cement hydration between cements from several manufactures. Table 1 illustrates results of physicochemical analysis performed on the cements tested.

TABLE 1

| Cement Type | Class A | Class C | Class G | Class H (1) | Class H (2) | Class H (3) | Type I | Type III |
|---|---|---|---|---|---|---|---|---|
| C3S | 55.3 | 70.47 | 48.02 | 47.11 | 45.66 | 59.66 | 59.5 | 16.69 |
| C2S | 17.49 | 3.41 | 26.03 | 27.18 | 28.6 | 18.2 | 13.07 | 23.39 |
| C34AF | 8.54 | 11.13 | 17.56 | 17.67 | 17.44 | 14.16 | 10.51 | 3.83 |
| C3A | 10.02 | 5.93 | 2.29 | 0 | 0 | 0.41 | 6.8 | 12.74 |
| gypsum | 5.22 | 5.63 | 3.98 | 4.63 | 4.7 | 4.94 | 5.71 | 5.88 |
| surface area (cm^2/g) | 280 | 418 | 329 | 254 | 285 | 303 | 391 | 548 |

The activation energy of each of the Portland cements in Table 1 was obtained from calorimetry data. Results of the calorimetric tests is shown in Table 2.

TABLE 2

| Cement Type | Activation Energy (j/mol) |
|---|---|
| Class A | 41163 |
| Class C | 40493 |
| Class G | 36333 |
| Class H (1) | 36505 |
| Class H (2) | 38811 |
| Class H (3) | 41987 |
| Type I | 41430 |
| Type III | 43599 |

The data from Table 1 and 2 was fit to a curve and an expression relating the activation energy to the material characteristics was developed. Equation 9 shows the results of the curve fitting.

$$E_a = 58476 - 1168 * C_4AF(\%) - 777 * C_3A(\%) \quad (9)$$

More generally, the activation energy may be expressed as equation 10.

$$E_a = f(\text{particle size}, BET, SSA, C_2S, C_3S, C_4AF, C_3A, CaSO_4, \text{gypsum}) \quad (10)$$

Figure 4:
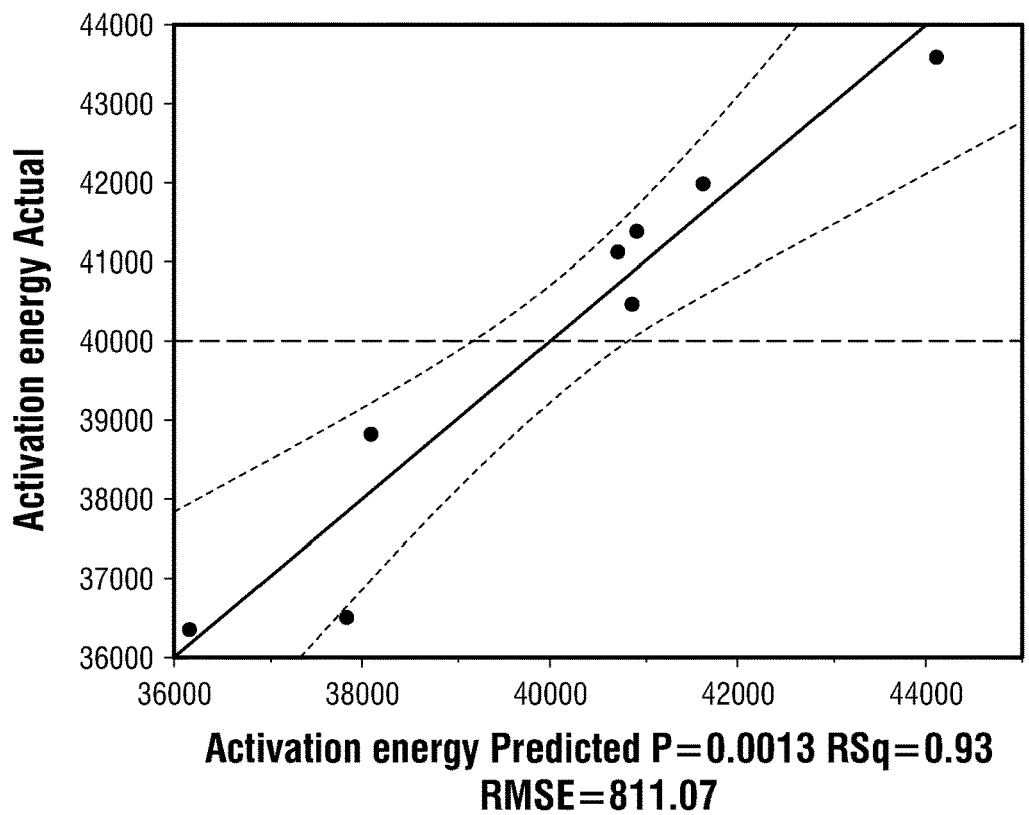
FIG. 4 illustrates a predicted activation energy from versus the observed activation energy.

FIG. 4 illustrates the predicted activation energy from equation 9 versus the observed activation energy.

Figure 5:
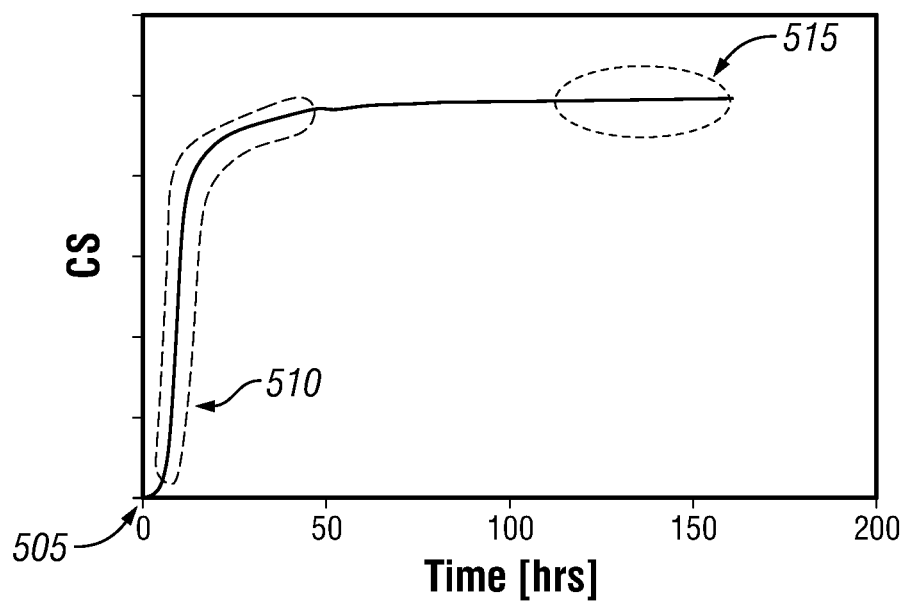
FIG. 5 illustrates a compressive strength development curve for a Portland cement slurry.

Portland cement slurries do not generally form compressive strength in a linear manner. FIG. 5 illustrates a typical compressive strength development curve for a Portland cement slurry. There are generally three zones in the time development of compressive strength. In FIG. 5, initial zone 505, also called the induction zone is where compressive strength builds minimally. The induction time may be a function of formulation and density. Rapid zone 510 is where initial rapid strength development occurs. Long term zone 515 is where long term slow strength development occurs. Compressive strength behavior in rapid zone 510 and long term zone 515 may be described by the Weibull function in equation 11.

$$\frac{CS}{CS_u} = 1 - \exp\left(-\left(\frac{t}{\lambda}\right)^\kappa\right) \quad (11)$$

Figure 6:
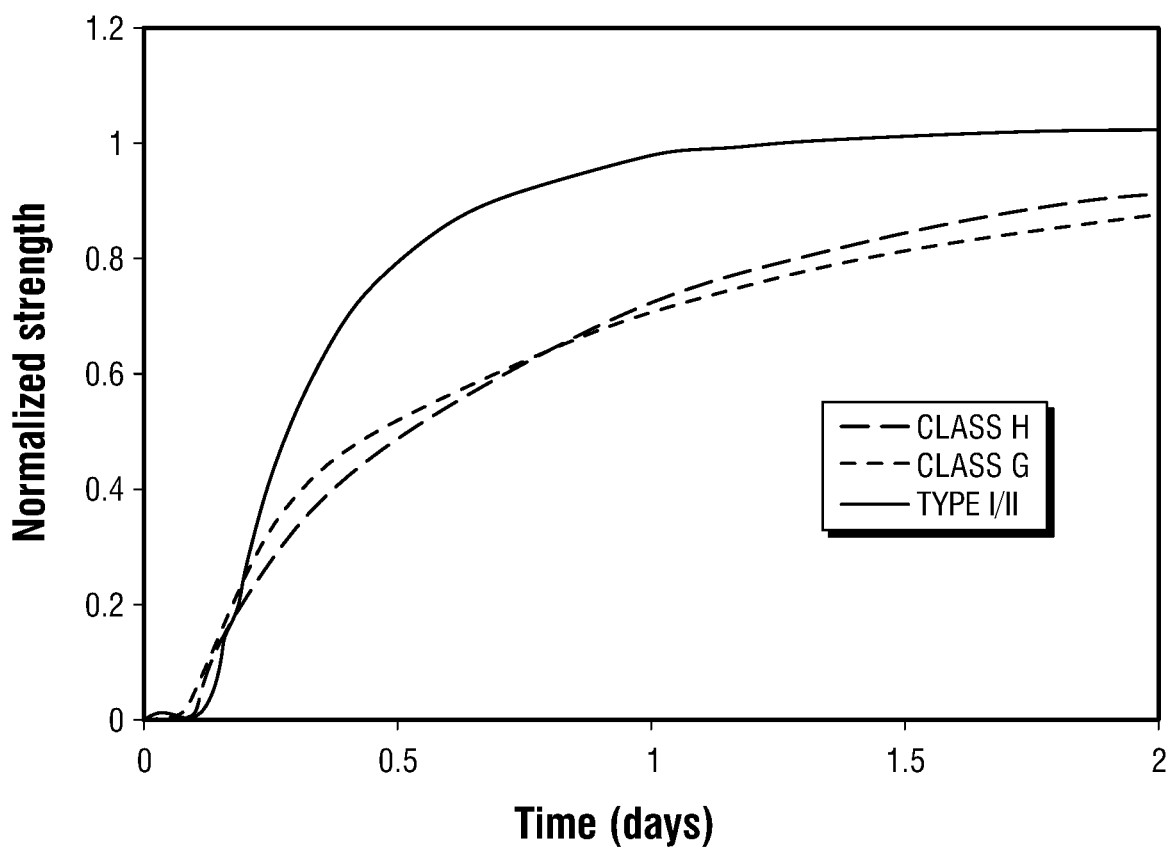
FIG. 6 illustrates a graph of compressive strength for a Weibull model of compressive strength.

In equation 11, CS is compressive strength of the cement slurry, Cu is the ultimate compressive strength, t is the time passed, $\lambda$ is the scale parameter of the Weibull function, and $\kappa$ is the shape parameter of the Weibull function. FIG. 6 illustrates results of applying two Weibull functions in series for three cement slurries and normalizing for the 7-day strength. The induction times and Weibull parameters are listed in Table 13. The Weibull parameters in Table 13 may be different for cements from different manufactures or regions. One of ordinary skill in the art, with the benefit of this disclosure, should be able to find Weibull parameters for any cement.

TABLE 13

| | $K_1$ | $\lambda_1^0$ (hrs) | $K_2$ | $\lambda_2^0$ (hrs) | tind (hrs) |
|---|---|---|---|---|---|
| Class H | 5.63 | 3.91 | 393 | 17.9 | 2.2 |
| Class G | 2.11 | 8361 | 0.77 | 18.19 | 1.7 |
| Type I/II | 5.35 | 4.45 | 1.34 | 8.45 | 2.45 |

In some examples, more than one Weibull function may be used to describe compressive strength development. For example, two, three, or more Weibull functions in series may be used to describe compressive strength development of Portland cement slurries. Equation 11 may also be modified to account for temperature dependence of compressive strength development in equation 12. In equation 12, $\lambda_0$ is the initial scale parameter and $\lambda(T)$ is the temperature dependent scale parameter represented by equation 13. $E_a$ is the activation energy which can be solved for using equations 9 or 10, R is the gas constant, $T_{ref}$ is a reference temperature, and T is the temperature.

$$\frac{CS}{CS_u} = 1 - \exp\left(-\left(\frac{t}{\lambda_0 * \lambda(T)}\right)^\kappa\right) \quad (12)$$

$$\lambda(T) = \exp\left(-\frac{E_a}{R}\left(\frac{1}{T_{ref}} - \frac{1}{T}\right)\right) \quad (13)$$

Equations 3, 8, 10, 11, 12, and 13 as well as the parameters in Table 3, allows compressive strength development for any neat Portland cement slurry to be predicted as a function of time and temperature. Equation 14 is a combination of the equations previously described which may be used to predict compressive strength development of a Portland cement slurry as a function of time and temperature.

$$CS = CS_0\left(\frac{w}{c_0}\right)^n * \begin{cases} \left(1 - \exp\left(\frac{t - t_{ind}}{\lambda_1^0 \lambda(T)}\right)^{\kappa_1}\right) & 0 \le t < t_1 \\ \left(1 - \exp\left(\frac{t - t_{ind}}{\lambda_2^0 \lambda(T)}\right)^{\kappa_2}\right) & t_1 \le t < t_2 \\ \vdots \end{cases} \quad (14)$$

In equation 14, $CS_0$ is a function of the Portland cement being used which may be calculated from equation 8, w is the mass fraction of water, $C_0$ is the mass fraction of Portland cement, n is a constant which may have a value of about −2.5, t is time, $t_{ind}$ is the induction time, $K_1$ and $K_2$ are the shape parameter or rate constant, $\lambda^0_1$ and $\lambda^0_2$ are the scale parameter or time scale parameter, and $\lambda(T)$ is the time scale correction factor for temperature dependence calculated by equation 13 and activation energy from equation 10. The above equations can be extended for any interval of time.

Although only some models of compressive strength have been illustrated herein, one of ordinary skill in the art, with the benefit of this disclosure should be able to derive other forms of the equations described herein without deviating from this disclosure. In addition, the techniques and equations described herein may also be applied to model cement slurries that contain reduced Portland cement, such as those slurries which contain other cementitious components in addition to Portland cement.

A method of designing a cement slurry may include obtaining samples of cementitious materials that may be included in a cement slurry and physicochemical characterizing the cementitious materials to determine a mineralogical composition, a surface area, specific surface area, a particle size, and others well known in the art. Downhole temperature and pressure may be provided by wellbore logs produced by measurements taken while drilling or by open hole logging techniques. Wellbore logs may provide data from which compressive strength requirements may be derived as well as time and temperature effects on the compressive strength development of a cement slurry. A cement recipe may include the identity and amounts of components to make a cement slurry. For a cement recipe, the ultimate strength may be predicted by equation 8 and equation 3 the activation energy may be predicted by equations 9 and 10. Weibull parameters may be determined for each of the cementitious components in the cement slurry recipe if not already known and thereafter, the time dependent compressive strength development may be estimated using equations 12 and 13. A model may be generated from a cement recipe and the model analyzed. A cement slurry may then be prepared according to the recipe if the step of analyzing the model meets a parameter. The results from each of the calculations may be entered into equation 14 and the compressive strength development may be estimated from density, temperature, and time. If the compressive strength development meets or exceeds the requirements derived previously, the cement slurry may be prepared and tested to verify the cement recipe meets all requirements. If the cement recipe does not meet the derived requirements, the slurry may be adjusted, for example, by increasing the density by decreasing the mass fraction of water or by including cement set retarders or cement set accelerators. The adjusted slurry may then be prepared and tested to see if the adjusted slurry meets all requirements. If the cement slurry meets the requirements, the cement slurry may be selected to be prepared and pumped into a subterranean formation.

The cement slurries described herein may include water and at least one cement component. The cement slurries may have a density suitable for a particular application. The cement slurries may have any suitable density, including, but not limited to, in the range of about 8 pounds per gallon ("ppg") (959 kg/m$^3$) to about 20 ppg (2397 kg/m$^3$). The water used in the cement slurries may include, for example, freshwater, saltwater (e.g., water containing one or more salts dissolved therein), brine (e.g., saturated saltwater produced from subterranean formations), seawater, or combinations thereof. Generally, the water may be from any source, provided that it does not contain an excess of compounds that may undesirably affect other components in the cement slurry. The water may be included in an amount sufficient to form a pumpable slurry. The water may be included in the cement slurries in any suitable range, including, but not limited to, in the range of about 40% to about 200% by weight of the cement component or components ("bwoc"). By weight of cement refers to the total weight of all cement components included in the cement slurry. In some examples, the water may be included in an amount in the range of about 40% to about 150% bwoc.

The cement slurry may include a hydraulic cement. A variety of hydraulic cements may be utilized in accordance with the present disclosure, including, but not limited to, those including calcium, aluminum, silicon, oxygen, iron, and/or sulfur, which set and harden by reaction with water. Suitable hydraulic cements may include Portland cements, gypsum, and calcium aluminate cements, among others. Portland cements may be classified as Classes A, C, G, and H cements according to American Petroleum Institute, API Specification for Materials and Testing for Well Cements, API Specification 10, Fifth Ed., Jul. 1, 1990. In addition, in some examples, cements suitable for use may be classified as ASTM Type I, II, or III. Where present, the hydraulic cement generally may be included in the cement slurries in an amount sufficient to provide the desired compressive strength and/or density. The hydraulic cement may be present in the cement slurries in any suitable amount, including, but not limited to, in the range of about 0% to about 99% bwoc. In some examples the hydraulic cement may be present in an amount ranging between any of and/or including any of about 1%, about 5%, about 10%, about 20%, about 40%, about 60%, about 80%, or about 90% bwoc. In addition, the cement slurries may also be designed that are free (or essentially free) of Portland cement. Those of ordinary skill in the art, with the benefit of this disclosure, should be able to select an appropriate amount of hydraulic cement for a particular application.

The cement slurry may include a geopolymer cement, which may include an aluminosilicate source, a metal silicate source, and an activator. The geopolymer cement may react to form a geopolymer. A geopolymer is an inorganic polymer that forms long-range, covalently bonded, non-crystalline networks. Geopolymers may be formed by chemical dissolution and subsequent re-condensation of various aluminosilicates and silicates to form a 3D-network or three-dimensional mineral polymer. The activator for the geopolymer cement may include, but is not limited to, metal hydroxides, chloride salts such as KCl, $CaCl_2$, NaCl, carbonates such as $Na_2CO_3$, silicates such as sodium silicate, aluminates such as sodium aluminate, and ammonium hydroxide. The aluminosilicate source for the geopolymer cement may include any suitable aluminosilicate. Aluminosilicate is a mineral including aluminum, silicon, and oxygen, plus counter-cations. A wide variety of suitable minerals may be an aluminosilicate source in that they may comprise aluminosilicate minerals. The metal silicate source may comprise any suitable metal silicate. A silicate is a compound containing an anionic silicon compound. Some examples of a silicate include the orthosilicate anion also known as silicon tetroxide anion, $SiO_4^{4-}$ as well as hexafluorosilicate $[SiF_6]^{2-}$. Other common silicates include cyclic and single chain silicates which may have the general formula $[SiO_{2+n}]^{2n-}$ and sheet-forming silicates $([SiO_{2.5}]^-)_n$. Each silicate example may have one or more metal cations associated with each silicate molecule. Some suitable metal silicate sources and may include, without limitation, sodium silicate, magnesium silicate, and potassium silicate. Where present, the geopolymer cement generally may be included in the cement slurries in an amount sufficient to provide the desired compressive strength and/or density. The geopolymer cement may be present in the cement slurries in any suitable amount, including, but not limited to, an amount in the range of about 0% to about 99% bwoc. In some examples the geopolymer cement may be present in an amount ranging between any of and/or including any of about 1%, about 5%, about 10%, about 20%, about 40%, about 60%, about 80%, or about 90% bwoc. One of ordinary skill in the art, with the benefit of this disclosure, would be able to select an appropriate amount of geopolymer cement for a particular application.

The cement slurries may include a silica source. Silica may also be referred to as silicon dioxide ($SiO_2$). By inclusion of a silica source, a different path may be used to arrive at a similar product as from Portland cement. For example, a pozzolanic reaction may be induced wherein silicic acid ($H_4SiO_4$) and portlandite ($Ca(OH)_2$) react to form a cement product (calcium silicate hydrate). If other compounds, such as, aluminate, are present in the silica source, additional reactions may occur to form additional cement products, such as calcium aluminate hydrates. Additionally, alumina (aluminum oxide $Al_2O_3$) may be present in the silica source. Calcium hydroxide necessary for the reaction may be provide from other cement components, such as Portland cement, or may be separately added to the cement slurry. Examples of suitable silica sources may include fly ash, slag, silica fume, crystalline silica, silica flour, cement kiln dust ("CKD"), volcanic rock, metakaolin, diatomaceous earth, zeolite, shale, and agricultural waste ash (e.g., rice husk ash, sugar cane ash, and bagasse ash), among other. Where present, the silica source generally may be included in the cement slurries in an amount sufficient to provide the desired compressive strength and/or density. The silica source may be present in the cement slurries in any suitable amount, including, but not limited to an amount in the range of about 0% to about 99% bwoc. In some examples the silica source may be present in an amount ranging between any of and/or including any of about 1%, about 5%, about 10%, about 20%, about 40%, about 60%, about 80%, or about 90% bwoc. Those of ordinary skill in the art, with the benefit of this disclosure, would be able to select an appropriate amount of silica source for a particular application.

The cement slurries may include slag. Slag is generally a by-product in the production of various metals from their corresponding ores. By way of example, the production of cast iron can produce slag as a granulated, blast furnace by-product with the slag generally including the oxidized impurities found in iron ore. Slag generally does not contain sufficient basic material, so slag cement may be used that further may comprise a base to produce a settable composition that may react with water to set to form a hardened mass. Examples of suitable sources of bases include, but are not limited to, sodium hydroxide, sodium bicarbonate, sodium carbonate, lime, and combinations thereof. The slag may be present in the cement slurries in any suitable amount, including, but not limited to an amount in the range of about 0% to about 99% bwoc. In some examples the slag may be present in an amount ranging between any of and/or including any of about 1%, about 5%, about 10%, about 20%, about 40%, about 60%, about 80%, or about 90% bwoc. Those of ordinary skill in the art, with the benefit of this disclosure, would be able to select an appropriate amount of slag for a particular application.

The cement slurries may include cement kin dust or "CKD." CKD refers to a partially calcined kiln feed which is removed from the gas stream and collected, for example, in a dust collector during the manufacture of cement. Usually, large quantities of CKD are collected in the production of cement that are commonly disposed of as waste. Disposal of the CKD as waste can add undesirable complexities to the manufacture of the cement, as well as the environmental concerns associated with its disposal. The CKD may be present in the cement slurries in any suitable amount, including, but not limited to an amount in the range of about 0% to about 99% bwoc. In some examples the CKD may be present in an amount ranging between any of and/or including any of about 1%, about 5%, about 10%, about 20%, about 40%, about 60%, about 80%, or about 90% bwoc. Those of ordinary skill in the art, with the benefit of this disclosure, would be able to select an appropriate amount of CKD for a particular application.

The cement slurries may include minerals such as natural glasses. Certain natural glasses may exhibit cementitious properties, in that it may set and harden in the presence of hydrated lime and water. Natural glasses may be present in the cement slurries in any suitable amount, including, but not limited to an amount in the range of about 0% to about 99% bwoc. In some examples the natural glasses may be present in an amount ranging between any of and/or including any of about 1%, about 5%, about 10%, about 20%, about 40%, about 60%, about 80%, or about 90% bwoc. Those of ordinary skill in the art, with the benefit of this disclosure, should be able to select an appropriate amount of silica source for a particular application.

Clays may be included in the cement slurries. Some clays may include shale or metakaolin. Among other things, clays included in the cement slurries may react with excess lime to form a suitable cementing material, for example, calcium silicate hydrate. A variety of clays are suitable, including those including silicon, aluminum, calcium, and/or magnesium. An example of a suitable shale comprises vitrified shale. Zeolites may also be included in the cement slurries. Zeolites generally are porous alumino-silicate minerals that may be either a natural or synthetic material. Synthetic zeolites are based on the same type of structural cell as natural zeolites and may comprise aluminosilicate hydrates. As used herein, the term "zeolite" refers to all natural and synthetic forms of zeolite. Examples of zeolites may include, without limitation, mordenite, zsm-5, zeolite x, zeolite y, zeolite a, etc. Furthermore, examples including zeolite may comprise zeolite in combination with a cation such as $Na^+$, $K^+$, $Ca^{2+}$, $Mg^{2+}$, etc. Zeolites including cations such as sodium may also provide additional cation sources to the cement slurry as the zeolites dissolve. The clays and zeolites may be present in the cement slurries in any suitable amount, including, but not limited to an amount in the range of about 0% to about 99% bwoc. In some examples the clays and zeolites may be present in an amount ranging between any of and/or including any of about 1%, about 5%, about 10%, about 20%, about 40%, about 60%, about 80%, or about 90% bwoc. Those of ordinary skill in the art, with the benefit of this disclosure, would be able to select an appropriate amount of clays and/or zeolite for a particular application.

The cement slurries may further include hydrated lime or calcium hydroxide. In some examples, the hydrated lime may be provided as quicklime (calcium oxide) which hydrates when mixed with water to form the hydrated lime. The hydrated lime may be included in examples of the cement slurries. Where present, the hydrated lime may be included in the cement slurries in an amount in the range of from about 10% to about 100% by weight of the silica source, for example. In some examples, the hydrated lime may be present in an amount ranging between any of and/or including any of about 10%, about 20%, about 40%, about 60%, about 80%, or about 100% by weight of the silica source. One of ordinary skill in the art, with the benefit of this disclosure, would recognize the appropriate amount of hydrated lime to include for a chosen application.

In some examples, the cement slurries may include a calcium source other than hydrated lime. In general, calcium and a high pH, for example a pH of 7.0 or greater, may be needed for certain cementitious reactions to occur. A potential advantage of hydrated lime may be that calcium ions and hydroxide ions are supplied in the same molecule. In another example, the calcium source may be $Ca(NO_3)_2$ or $CaCl_2$ with the hydroxide being supplied form NaOH or KOH, for example. The calcium source and hydroxide source may be included in a silica source-to-hydrated-lime weight ratio of about 10:1 to about 1:1 or a ratio of about 3:1 to about 5:1. Where present, the alternate calcium source and hydroxide source may be included in the cement slurries in an amount in the range of from about 10% to about 100% by weight of the silica source, for example. In some examples, the alternate calcium source and hydroxide source may be present in an amount ranging between any of and/or including any of about 10%, about 20%, about 40%, about 60%, about 80%, or about 100% by weight of the silica source. One of ordinary skill in the art, with the benefit of this disclosure, would recognize the appropriate amount of alternate calcium source and hydroxide source to include for a chosen application.

The cement slurries may include cement additives that may impart desirable properties to the cementing slurry. Examples of such additives include, but are not limited to: weighting agents, retarders, accelerators, activators, gas control additives, lightweight additives, gas-generating additives, mechanical-property-enhancing additives, lost-circulation materials, filtration-control additives, fluid-loss-control additives, defoaming agents, foaming agents, dispersants, thixotropic additives, suspending agents, and combinations thereof. One of ordinary skill in the art, with the benefit of this disclosure, would be able to select an appropriate additive for a particular application.

The cement slurries disclosed herein may be used in a variety of subterranean applications, including primary and remedial cementing. The cement slurries may be introduced into a subterranean formation and allowed to set. In primary cementing applications, for example, the cement slurries may be introduced into the annular space between a conduit located in a wellbore and the walls of the wellbore (and/or a larger conduit in the wellbore), wherein the wellbore penetrates the subterranean formation. The cement slurry may be allowed to set in the annular space to form an annular sheath of hardened cement. The cement slurry may form a barrier that prevents the migration of fluids in the wellbore. The cement composition may also, for example, support the conduit in the wellbore. In remedial cementing applications, the cement compositions may be used, for example, in squeeze cementing operations or in the placement of cement plugs. By way of example, the cement compositions may be placed in a wellbore to plug an opening (e.g., a void or crack) in the formation, in a gravel pack, in the conduit, in the cement sheath, and/or between the cement sheath and the conduit (e.g., a micro annulus).

Figure 7:
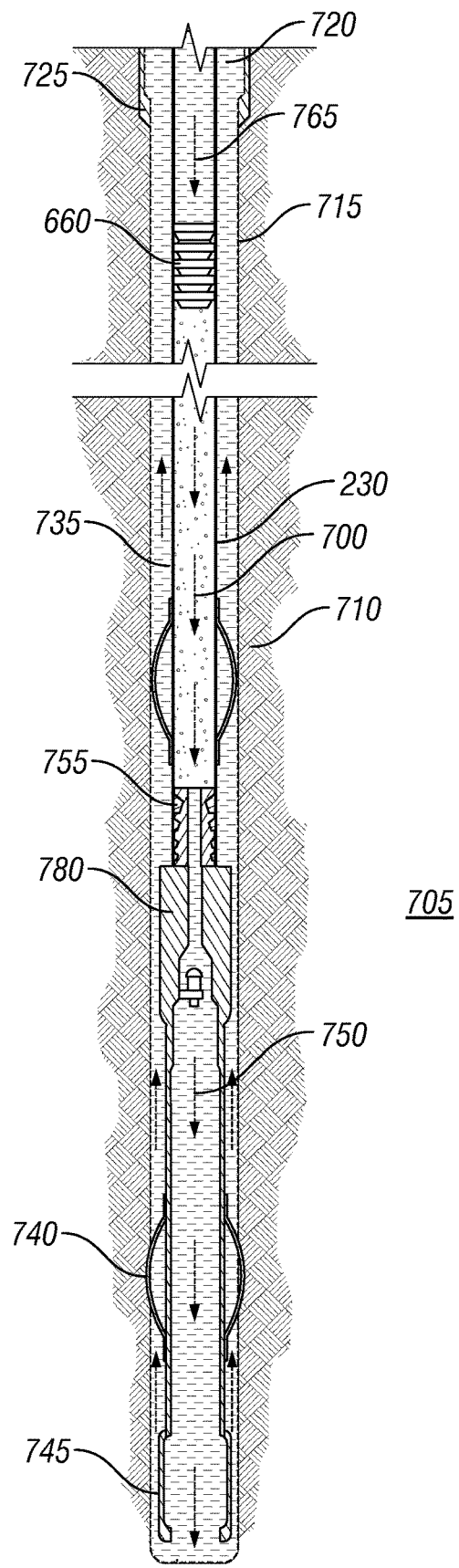
FIG. 7 illustrates introduction of a cement slurry into a wellbore.

Reference is now made to FIG. 7, illustrating use of a cement slurry 700. Cement slurry 700 may comprise any of the components described herein. Cement slurry 700 may be designed, for example, using reactivity mapping as described herein. Turning now to FIG. 6, the cement slurry 700 may be placed into a subterranean formation 705 in accordance with example systems, methods and cement slurries. As illustrated, a wellbore 710 may be drilled into the subterranean formation 705. While wellbore 710 is shown extending generally vertically into the subterranean formation 705, the principles described herein are also applicable to wellbores that extend at an angle through the subterranean formation 705, such as horizontal and slanted wellbores. As illustrated, the wellbore 710 comprises walls 715. In the illustration, a surface casing 220 has been inserted into the wellbore 710. The surface casing 220 may be cemented to the walls 715 of the wellbore 710 by cement sheath 720. In the illustration, one or more additional conduits (e.g., intermediate casing, production casing, liners, etc.), shown here as casing 730 may also be disposed in the wellbore 710. As illustrated, there is a wellbore annulus 735 formed between the casing 730 and the walls 715 of the wellbore 710 and/or the surface casing 725. One or more centralizers 740 may be attached to the casing 730, for example, to centralize the casing 730 in the wellbore 710 prior to and during the cementing operation.

With continued reference to FIG. 7, the cement slurry 700 may be pumped down the interior of the casing 730. The cement slurry 700 may be allowed to flow down the interior of the casing 730 through the casing shoe 745 at the bottom of the casing 730 and up around the casing 730 into the wellbore annulus 735. The cement slurry 700 may be allowed to set in the wellbore annulus 735, for example, to form a cement sheath that supports and positions the casing 730 in the wellbore 710. While not illustrated, other techniques may also be utilized for introduction of the cement slurry 700. By way of example, reverse circulation techniques may be used that include introducing the cement slurry 700 into the subterranean formation 705 by way of the wellbore annulus 735 instead of through the casing 730. As it is introduced, the cement slurry 700 may displace other fluids 750, such as drilling fluids and/or spacer fluids that may be present in the interior of the casing 730 and/or the wellbore annulus 735. While not illustrated, at least a portion of the displaced fluids 250 may exit the wellbore annulus 735 via a flow line and be deposited, for example, in one or more retention pits. A bottom plug 755 may be introduced into the wellbore 710 ahead of the cement slurry 700, for example, to separate the cement slurry 700 from the fluids 550 that may be inside the casing 730 prior to cementing. After the bottom plug 755 reaches the landing collar 780, a diaphragm or other suitable device should rupture to allow the cement slurry 700 through the bottom plug 755. The bottom plug 755 is shown on the landing collar 780. In the illustration, a top plug 760 may be introduced into the wellbore 710 behind the cement slurry 700. The top plug 760 may separate the cement slurry 700 from a displacement fluid 765 and also push the cement slurry 700 through the bottom plug 755.

Figure 8:
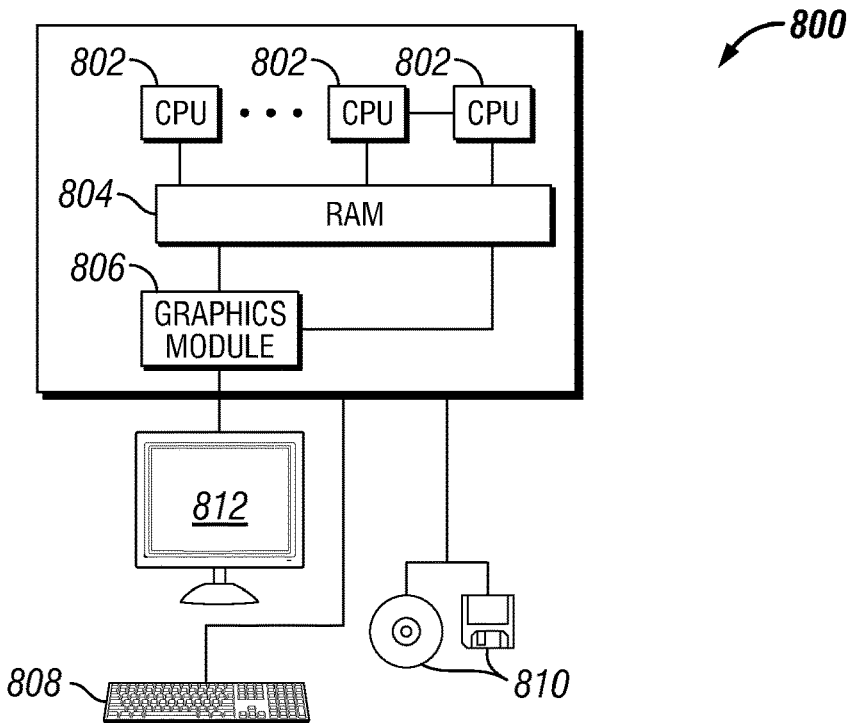
FIG. 8 is a schematic illustration of an example of an information handling system.

FIG. 8 generally illustrates an example of an information handling system 800 that may include any instrumentality or aggregate of instrumentalities operable to compute, estimate, classify, process, transmit, receive, retrieve, originate, switch, store, display, manifest, detect, record, reproduce, handle, or utilize any form of information, intelligence, or data for business, scientific, control, or other purposes. For example, an information handling system 800 may be a personal computer, a network storage device, or any other suitable device and may vary in size, shape, performance, functionality, and price. In examples, information handling system 100 may be referred to as a supercomputer or a graphics supercomputer.

As illustrated, information handling system 800 may include one or more central processing units (CPU) or processors 802. Information handling system 800 may also include a random-access memory (RAM) 804 that may be accessed by processors 802. It should be noted information handling system 800 may further include hardware or software logic, ROM, and/or any other type of nonvolatile memory. Information handling system 800 may include one or more graphics modules 806 that may access RAM 804. Graphics modules 806 may execute the functions carried out by a Graphics Processing Module (not illustrated), using hardware (such as specialized graphics processors) or a combination of hardware and software. A user input device 808 may allow a user to control and input information to information handling system 800. Additional components of the information handling system 800 may include one or more disk drives, output devices 812, such as a video display, and one or more network ports for communication with external devices as well as a user input device 808 (e.g., keyboard, mouse, etc.). Information handling system 800 may also include one or more buses operable to transmit communications between the various hardware components.

Alternatively, systems and methods of the present disclosure may be implemented, at least in part, with non-transitory computer-readable media. Non-transitory computer-readable media may include any instrumentality or aggregation of instrumentalities that may retain data and/or instructions for a period of time. Non-transitory computer-readable media may include, for example, storage media 810 such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such wires, optical fibers, microwaves, radio waves, and other electromagnetic and/or optical carriers; and/or any combination of the foregoing.

Figure 9:
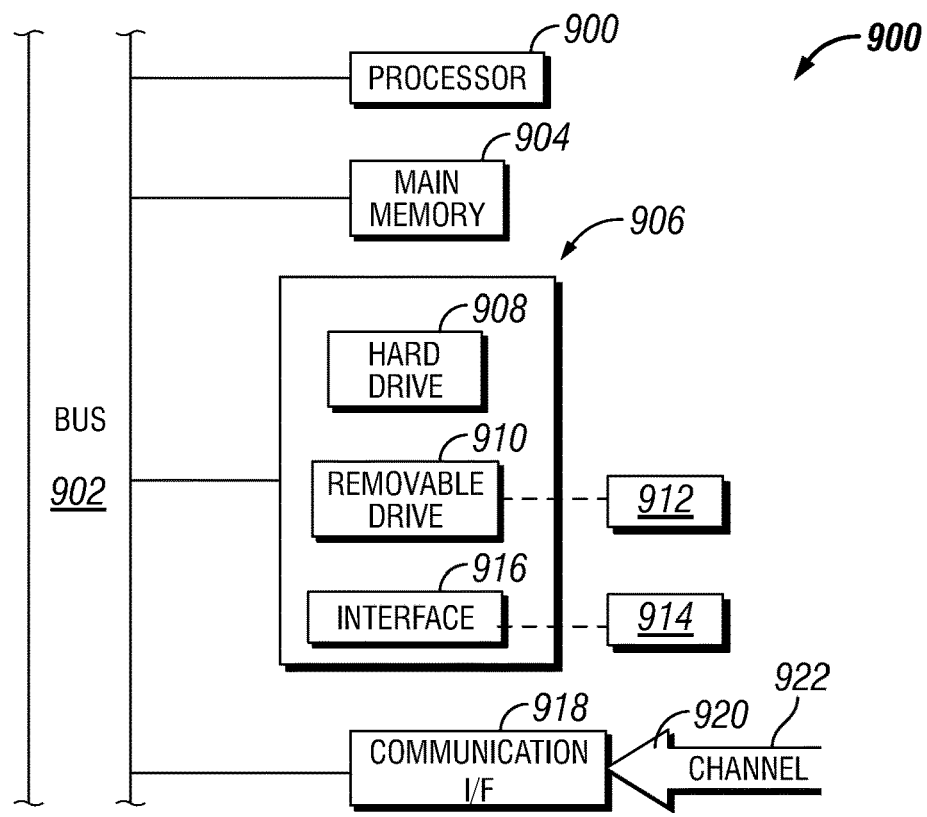
FIG. 9 illustrates additional detail of an information handling system.

FIG. 9 illustrates additional detail of information handling system 800. For example, information handling system 800 may include one or more processors, such as processor 900. Processor 900 may be connected to a communication bus 902. Various software embodiments are described in terms of this exemplary computer system. After reading this description, it will become apparent to a person skilled in the relevant art how to implement the example embodiments using other computer systems and/or computer architectures.

Information handling system 800 may also include a main memory 904, preferably random-access memory (RAM), and may also include a secondary memory 906. Secondary memory 906 may include, for example, a hard disk drive 908 and/or a removable storage drive 910, representing a floppy disk drive, a magnetic tape drive, an optical disk drive, etc. Removable storage drive 910 may read from and/or writes to a removable storage unit 912 in any suitable manner. Removable storage unit 912, represents a floppy disk, magnetic tape, optical disk, etc. which is read by and written to by removable storage drive 910. As will be appreciated, removable storage unit 912 includes a computer usable storage medium having stored therein computer software and/or data.

In alternative embodiments, secondary memory 906 may include other operations for allowing computer programs or other instructions to be loaded into information handling system 800. For example, a removable storage unit 914 and an interface 916. Examples of such may include a program cartridge and cartridge interface (such as that found in video game devices), a removable memory chip (such as an EPROM, or PROM) and associated socket, and other removable storage units 914 and interfaces 916 which may allow software and data to be transferred from removable storage unit 914 to information handling system 800.

In examples, information handling system 800 may also include a communications interface 918. Communications interface 918 may allow software and data to be transferred between information handling system 800 and external devices. Examples of communications interface 918 may include a modem, a network interface (such as an Ethernet card), a communications port, a PCMCIA slot and card, etc. Software and data transferred via communications interface 918 are in the form of signals 920 that may be electronic, electromagnetic, optical or other signals capable of being received by communications interface 918. Signals 920 may be provided to communications interface via a channel 922. Channel 922 carries signals 920 and may be implemented using wire or cable, fiber optics, a phone line, a cellular phone link, an RF link and/or any other suitable communications channels. For example, information handling system 800 includes at least one memory 904 operable to store computer-executable instructions, at least one communications interface 902, 918 to access the at least one memory 904; and at least one processor 900 configured to access the at least one memory 904 via the at least one communications interface 902, 918 and execute computer-executable instructions.

In this document, the terms "computer program medium" and "computer usable medium" are used to generally refer to media such as removable storage unit 912, a hard disk installed in hard disk drive 908, and signals 920. These computer program products may provide software to computer system 800.

Computer programs (also called computer control logic) may be stored in main memory 904 and/or secondary memory 906. Computer programs may also be received via communications interface 918. Such computer programs, when executed, enable information handling system 800 to perform the features of the example embodiments as discussed herein. In particular, the computer programs, when executed, enable processor 900 to perform the features of the example embodiments. Accordingly, such computer programs represent controllers of information handling system 800.

In examples with software implementation, the software may be stored in a computer program product and loaded into information handling system 800 using removable storage drive 910, hard disk drive 908 or communications interface 918. The control logic (software), when executed by processor 900, causes processor 900 to perform the functions of the example embodiments as described herein.

In examples with hardware implementation, hardware components such as application specific integrated circuits (ASICs). Implementation of such a hardware state machine so as to perform the functions described herein will be apparent to persons skilled in the relevant art(s). It should be noted that the disclosure may be implemented at least partially on both hardware and software.

The methods described herein may be carried out, at least in part, using a computer system including a computer-accessible medium, the computer-accessible medium containing a computer program that causes a processor to execute instructions that carry out at least some of the method steps described herein. In general, a computer-accessible medium may include any tangible or non-transitory storage media or memory media such as electronic, magnetic, or optical media—e.g., disk or CD/DVD-ROM coupled to the computer. The terms "tangible" and "non-transitory," as used herein, are intended to describe a computer-readable storage medium (or "memory") excluding propagating electromagnetic signals, but are not intended to otherwise limit the type of physical computer-readable storage device that is encompassed by the phrase computer-readable medium or memory. For instance, the terms "non-transitory computer-readable medium" or "tangible memory" are intended to encompass types of storage devices that do not necessarily store information permanently, including for example, random access memory (RAM), flash memory, or other volatile memory types. Program instructions and data stored on a tangible computer-accessible storage medium in non-transitory form may further be transmitted by transmission media or signals such as electrical, electromagnetic, or digital signals, which may be conveyed via a communication medium such as a network and/or a wireless link.

The following statements may describe certain embodiments of the disclosure but should be read to be limiting to any particular embodiment.

Statement 1. A method of designing a cement slurry comprising: providing a cement slurry recipe comprising water and at least one cementitious component; creating a model of a compressive strength of the cement recipe for a given time; preparing a cement slurry based at least in part on the model; and introducing the cement slurry into a subterranean formation.

Statement 2. The method of statement 1 wherein the step of creating the model comprises at least one of modeling an ultimate compressive strength of the cement recipe, modeling an activation energy of the cement recipe, and modeling a time dependency of compressive strength of the cement recipe.

Statement 3. The method of any of statements 1-2 wherein the step of creating a model comprises modeling an ultimate compressive strength of the cement recipe, and wherein the modeling the ultimate compressive strength comprises correlating at least one of water requirement of the cement recipe, specific gravity of the cement recipe, average particle size of the cement recipe, BET surface area of the cement recipe, specific surface area, concentration of $C_2S$ in the cement recipe, concentration of $C_3S$ in the cement recipe, concentration of $C_4AF$ in the cement recipe, concentration of $C_3A$ in the cement recipe, concentration of $CaSO_4$ in the cement recipe, and concentration of gypsum in the cement recipe to ultimate compressive strength.

Statement 4. The method of any of statements 1-3 wherein the step of creating a model comprises modeling an ultimate compressive strength of the cement recipe, and wherein the modeling the ultimate compressive strength comprises the following model:

$$CS = CS_0 \left(\frac{w}{c}\right)^n$$

where CS is ultimate compressive strength, $CS_0$ the ultimate compressive strength when a water to cement ratio is 1, w is a mass fraction of water, c is a mass fraction of cement, and n is a constant.

Statement 5. The method of any of statements 1-4 wherein the step of creating a model comprising modeling an activation energy of the cement recipe, and wherein the modeling the activation energy comprises correlating at least one of average particle size of the cement recipe, BET surface area of the cement recipe, specific surface area, concentration of $C_2S$ in the cement recipe, concentration of $C_3S$ in the cement recipe, concentration of $C_4AF$ in the cement recipe, concentration of $C_3A$ in the cement recipe, concentration of $CaSO_4$ in the cement recipe, and concentration of gypsum in the cement recipe to activation energy.

Statement 6. The method of any of statements 1-5 wherein the step of creating a model comprises modeling an activation energy of the cement recipe, and wherein the modeling the activation energy comprises correlating calorimetric data to the activation energy.

Statement 7. The method of any of statements 1-6 wherein the step of creating a model comprises modeling a time dependency of compressive strength of the cement recipe, and wherein the modeling the time dependency of compressive strength comprises correlating the compressive strength over time using a Weibull function.

Statement 8. The method of any of statements 1-7 wherein the step of creating a model comprises modeling a time dependency of compressive strength of the cement recipe, and wherein the modeling the time dependency of compressive strength comprises the following model:

$$\frac{CS}{CS_u} = 1 - \exp\left(-\left(\frac{t}{\lambda_0 * \exp\left(-\frac{E_a}{R}\left(\frac{1}{T_{ref}} - \frac{1}{T}\right)\right)}\right)^\kappa\right)$$

where CS is compressive strength, $CS_u$, t is time passed, $\lambda_0$ is an initial scale parameter, Ea is activation energy, R is a gas constant, $T_{ref}$ is a reference temperature, T is a temperature, and κ is s shape parameter.

Statement 9. The method of any of statements 1-8 wherein the step of modeling comprises the following model:

$$CS = CS_0 \left(\frac{w}{c_0}\right)^n * \begin{cases} \left(1 - \exp\left(\frac{t - t_{ind}}{\lambda_1^0 \lambda(T)}\right)^{\kappa_1}\right) & 0 \leq t < t_1 \\ \left(1 - \exp\left(\frac{t - t_{ind}}{\lambda_2^0 \lambda(T)}\right)^{\kappa_2}\right) & t_1 \leq t < t_2 \\ \vdots \end{cases}$$

where $CS_0$ is a function of Portland cement, w is a mass fraction of water, $C_0$ is a mass fraction of Portland cement, $Min_j$ is $\lambda_1^0$ and $\lambda_2^0$ are a scale parameter, $\lambda(T)$ is a temperature dependent scale parameter, t is time, $t_{ind}$ is induction time, and, $K_1$ and $K_2$ are a shape parameter.

Statement 10. The method of any of statements 1-9 further comprising providing a required ultimate compressive strength and a required time dependent compressive strength and comparing the required ultimate compressive strength and the required time dependent compressive strength to an output of the step of modeling.

Statement 11. The method of any of statements 1-10 further comprising adjusting a concentration of the water, the at least one cementitious component, or both, in the cement recipe.

Statement 12. A non-transitory computer readable medium having data stored therein representing software executable by a computer, the software including instructions comprising: instructions to calculate a compressive strength of a cement slurry using a model of compressive strength.

Statement 13. The non-transitory computer readable medium of statement 12 wherein cement slurry comprises water and at least one cementitious component.

Statement 14. The non-transitory computer readable medium of any of statements 12-13 wherein the model of compressive strength comprises a Weibull function.

Statement 15. The non-transitory computer readable medium of any of statements 12-14 wherein the model of compressive strength comprises a model of at least one of a model of a cement ultimate compressive strength, a model of a cement activation energy, and a model of time dependency of cement compressive strength.

Statement 16. A method of cementing comprising: providing a cement recipe comprising water and at least one cementitious component, wherein the at least one cementitious component comprises Portland cement; modeling a compressive strength and a time dependent compressive strength of the cement recipe using a cement compressive strength model; comparing the compressive strength and the time dependent compressive strength of the cement recipe to an ultimate compressive strength requirement and a time dependent compressive strength requirement; preparing the cement recipe; and placing the cement recipe in a subterranean formation.

Statement 17. The method of statement 16 wherein the cement compressive strength model comprises a Weibull function.

Statement 18. The method of any of statements 16-17 wherein the step of modeling the compressive strength of the cement recipe comprises modeling the following function:

$$CS = CS_0 \left(\frac{w}{c}\right)^n$$

where CS is compressive strength, $CS_0$ the ultimate compressive strength when a water to cement ratio is 1, w is a mass fraction of water, c is a mass fraction of cement, and n is a constant.

Statement 19. The method of any of statements 16-18 wherein the step of modeling the time dependent compressive strength of the cement recipe comprises modeling the following function:

$$CS = CS_0 \left(\frac{w}{c_0}\right)^n * \begin{cases} \left(1 - \exp\left(\frac{t - t_{ind}}{\lambda_1^0 \lambda(T)}\right)^{\kappa_1}\right) & 0 \leq t < t_1 \\ \left(1 - \exp\left(\frac{t - t_{ind}}{\lambda_2^0 \lambda(T)}\right)^{\kappa_2}\right) & t_1 \leq t < t_2 \\ \vdots \end{cases}$$

were $CS_0$ is a function of Portland cement, w is a mass fraction of water, $C_0$ is a mass fraction of Portland cement, $Min_j$ is $\lambda_1^0$ and $\lambda_2^0$ are a scale parameter, $\lambda(T)$ is a temperature dependent scale parameter, t is time, $t_{ind}$ is induction time, and, $K_1$ and $K_2$ are a shape parameter.

Statement 20. The method of any of statements 16-19 further comprising adjusting at least one of a concentration of the water, a concentration of the at least one cementitious component, or both based at least in part on a result of the step of comparing.

The disclosed cement compositions and associated methods may directly or indirectly affect any pumping systems, which representatively includes any conduits, pipelines, trucks, tubulars, and/or pipes which may be coupled to the pump and/or any pumping systems and may be used to fluidically convey the cement compositions downhole, any pumps, compressors, or motors (e.g., topside or downhole) used to drive the cement compositions into motion, any valves or related joints used to regulate the pressure or flow rate of the cement compositions, and any sensors (i.e., pressure, temperature, flow rate, etc.), gauges, and/or combinations thereof, and the like. The cement compositions may also directly or indirectly affect any mixing hoppers and retention pits and their assorted variations.

It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the elements that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present disclosure is well adapted to attain the ends and advantages mentioned as well as those that are inherent therein. The particular examples disclosed above are illustrative only, as the present disclosure may be modified and practiced in different but equivalent manners apparent to those skilled in the art having the benefit of the teachings herein. Although individual examples are discussed, the disclosure covers all combinations of all those examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of the present disclosure. If there is any conflict in the usages of a word or term in this specification and one or more patent(s) or other documents that may be incorporated herein by reference, the definitions that are consistent with this specification should be adopted.

What is claimed is:

1. A method of designing a cement slurry comprising:
providing a cement slurry recipe comprising water and at least one cementitious component, a required ultimate compressive strength, and a required time dependent compressive strength;
creating a model of a compressive strength of the cement recipe for a given time and comparing the required ultimate compressive strength and the required time dependent compressive strength to an output of the step of modeling;
preparing a cement slurry based at least in part on the model; and
introducing the cement slurry into a subterranean formation.

2. The method of claim 1 wherein the step of creating the model comprises at least one of modeling an ultimate compressive strength of the cement recipe, modeling an activation energy of the cement recipe, and modeling a time dependency of compressive strength of the cement recipe.

3. The method of claim 1 wherein the step of creating a model comprises modeling an ultimate compressive strength of the cement recipe, wherein the cement recipe further comprises portland cement and gypsum, and wherein the modeling the ultimate compressive strength comprises correlating at least one of water requirement of the cement recipe, specific gravity of the cement recipe, average particle size of the cement recipe, BET surface area of the cement recipe, specific surface area, concentration of $C_2S$ in the cement recipe, concentration of $C_3S$ in the cement recipe, concentration of $C_4AF$ in the cement recipe, concentration of $C_3A$ in the cement recipe, concentration of $CaSO_4$ in the cement recipe, and concentration of gypsum in the cement recipe to ultimate compressive strength.

4. The method of claim 1 wherein the step of creating a model comprises modeling an ultimate compressive strength of the cement recipe, and wherein the modeling the ultimate compressive strength comprises the following model:

$$CS = CS_0 \left(\frac{w}{c}\right)^n$$

where CS is ultimate compressive strength, $CS_0$ the ultimate compressive strength when a water to cement ratio is 1, w is a mass fraction of water, c is a mass fraction of cement, and n is a constant.

5. The method of claim 1 wherein the step of creating a model comprising modeling an activation energy of the cement recipe, wherein the cement recipe further comprises portland cement and gypsum, and wherein the modeling the activation energy comprises correlating at least one of average particle size of the cement recipe, BET surface area of the cement recipe, specific surface area, concentration of $C_2S$ in the cement recipe, concentration of $C_3S$ in the cement recipe, concentration of $C_4AF$ in the cement recipe, concentration of $C_3A$ in the cement recipe, concentration of $CaSO_4$ in the cement recipe, and concentration of gypsum in the cement recipe to activation energy.

6. The method of claim 1 wherein the step of creating a model comprises modeling an activation energy of the cement recipe, and wherein the modeling the activation energy comprises correlating calorimetric data to the activation energy.

7. The method of claim 1 wherein the step of creating a model comprises modeling a time dependency of compressive strength of the cement recipe, and wherein the modeling the time dependency of compressive strength comprises correlating the compressive strength over time using a Weibull function.

8. The method of claim 1 wherein the step of creating a model comprises modeling a time dependency of compressive strength of the cement recipe, and wherein the modeling the time dependency of compressive strength comprises the following model:

$$\frac{cs}{cs_u} = 1 - \exp\left(-\left(\frac{t}{\lambda_0 * \exp\left(\frac{E_a}{R}\left(\frac{11}{\tau_{ref}\tau}\right)\right)}\right)^\kappa\right)$$

where CS is compressive strength, $CS_u$, t is time passed, $\lambda_0$ is an initial scale parameter, Ea is activation energy, R is a gas constant, $T_{ref}$ is a reference temperature, T is a temperature, and κ is s shape parameter.

9. The method of claim 1 wherein the step of modeling comprises the following model:

$$CS = CS_0\left(\frac{w}{c_0}\right)^n * \begin{cases} \left(1 - \exp\left(\frac{t - t_{ind}}{\lambda_1^0 \lambda(T)}\right)^{\kappa_1}\right) & 0 \leq t < t_1 \\ \left(1 - \exp\left(\frac{t - t_{ind}}{\lambda_2^0 \lambda(T)}\right)^{\kappa_2}\right) & t_1 \leq t < t_2 \\ \vdots \end{cases}$$

where $CS_0$ is a function of Portland cement, w is a mass fraction of water, $C_0$ is a mass fraction of Portland cement, $Min_j$ is $\lambda^0_1$ and $\lambda^0_2$ are a scale parameter, $\lambda(T)$ is a temperature dependent scale parameter, t is time, $t_{ind}$ is induction time, and, $K_1$ and $K_2$ are a shape parameter.

10. The method of claim 1 further comprising adjusting a concentration of the water, the at least one cementitious component, or both, in the cement recipe.

11. A method of cementing comprising:
providing a cement recipe comprising water and at least one cementitious component, wherein the at least one cementitious component comprises Portland cement;

modeling a compressive strength and a time dependent compressive strength of the cement recipe using a cement compressive strength model;

comparing the compressive strength and the time dependent compressive strength of the cement recipe to an ultimate compressive strength requirement and a time dependent compressive strength requirement;

preparing the cement recipe; and placing the cement recipe in a subterranean formation.

12. The method of claim 11 wherein the cement compressive strength model comprises a Weibull function.

13. The method of claim 11 wherein the step of modeling the compressive strength of the cement recipe comprises modeling the following function:

$$CS = CS_0 \left(\frac{w}{c}\right)^n$$

where CS is compressive strength, $CS_0$ the ultimate compressive strength when a water to cement ratio is 1, w is a mass fraction of water, c is a mass fraction of cement, and n is a constant.

14. The method of claim 11 wherein the step of modeling the time dependent compressive strength of the cement recipe comprises modeling the following function:

$$CS = CS_0 \left(\frac{w}{C_0}\right)^n * \begin{cases} \left(1 - \exp\left(\frac{t - t_{ind}}{\lambda_1^0 \lambda(T)}\right)^{K_1}\right) & 0 \leq t < t_1 \\ \left(1 - \exp\left(\frac{t - t_{ind}}{\lambda_2^0 \lambda(T)}\right)^{K_2}\right) & t_1 \leq t < t_2 \\ \vdots \end{cases}$$

where $CS_0$ is a function of Portland cement, w is a mass fraction of water, $C_0$ is a mass fraction of Portland cement, $Min_j$ is $\lambda_1^0$ and $\lambda_2^0$ are a scale parameter, $\lambda(T)$ is a temperature dependent scale parameter, t is time, $t_{ind}$ is induction time, and, $K_1$ and $K_2$ are a shape parameter.

15. The method of claim 11 further comprising adjusting at least one of a concentration of the water, a concentration of the at least one cementitious component, or both based at least in part on a result of the step of comparing.

16. A method of designing a cement slurry comprising:
providing a cement slurry recipe comprising water and at least one cementitious component;

creating a model of a compressive strength of the cement recipe for a given time, wherein the step of creating a model comprises modeling a time dependency of compressive strength of the cement recipe, and wherein the modeling the time dependency of compressive strength comprises the following model:

$$\frac{CS}{CS_u} = 1 - \exp\left(-\left(\frac{t}{\lambda_0 * \exp\left(-\frac{E_a}{R}\left(\frac{1}{T_{ref}} - \frac{1}{T}\right)\right)}\right)^\kappa\right)$$

where CS is compressive strength, $CS_u$, t is time passed, $\lambda_0$ is an initial scale parameter, Ea is activation energy, R is a gas constant, $T_{ref}$ is a reference temperature, T is a temperature, and κ is s shape parameter;

preparing a cement slurry based at least in part on the model; and introducing the cement slurry into a subterranean formation.

17. A method of designing a cement slurry comprising:
providing a cement slurry recipe comprising water and at least one cementitious component;

creating a model of a compressive strength of the cement recipe for a given time, wherein the step of modeling comprises the following model:

$$CS = CS_0 \left(\frac{w}{C_0}\right)^n * \begin{cases} \left(1 - \exp\left(\frac{t - t_{ind}}{\lambda_1^0 \lambda(T)}\right)^{K_1}\right) & 0 \leq t < t_1 \\ \left(1 - \exp\left(\frac{t - t_{ind}}{\lambda_2^0 \lambda(T)}\right)^{K_2}\right) & t_1 \leq t < t_2 \\ \vdots \end{cases}$$

where $CS_0$ is a function of Portland cement, w is a mass fraction of water, $C_0$ is a mass fraction of Portland cement, $Min_j$ is $\lambda_1^0$ and $\lambda_2^0$ are a scale parameter, $\lambda(T)$ is a temperature dependent scale parameter, t is time, $t_{ind}$ is induction time, and, $K_1$ and $K_2$ are a shape parameter;

preparing a cement slurry based at least in part on the model; and introducing the cement slurry into a subterranean formation.

* * * * *

UNITED STATES PATENT AND TRADEMARK OFFICE
CERTIFICATE OF CORRECTION

PATENT NO. : 11,198,649 B2
APPLICATION NO. : 16/633411
DATED : December 14, 2021
INVENTOR(S) : John Paul Bir Singh, Thomas Jason Pisklak and Ronnie Glen Morgan Page 1 of 1

It is certified that error appears in the above-identified patent and that said Letters Patent is hereby corrected as shown below:

In the Claims

Column 20, Lines 35-40, should read:

$$\frac{CS}{CS_u} = 1 - \exp\left(-\left(\frac{t}{\lambda_0 * \exp\left(-\frac{E_a}{R}\left(\frac{1}{T_{ref}} - \frac{1}{T}\right)\right)}\right)^K\right)$$

Signed and Sealed this
Twenty-second Day of March, 2022

Drew Hirshfeld
*Performing the Functions and Duties of the*
*Under Secretary of Commerce for Intellectual Property and*
*Director of the United States Patent and Trademark Office*